(12) United States Patent
Gupta et al.

(10) Patent No.: US 6,280,740 B1
(45) Date of Patent: Aug. 28, 2001

(54) FORMULATIONS OF RECOMBINANT PAPILLOMAVIRUS VACCINES

(75) Inventors: Sunil K. Gupta, Piscataway, NJ (US); George E. Mark, III, Newtown, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/331,290

(22) Filed: Jan. 14, 2000

Related U.S. Application Data

(63) Continuation of application No. 08/992,450, filed on Dec. 17, 1997, now abandoned.
(60) Provisional application No. 60/033,566, filed on Dec. 20, 1996.

(51) Int. Cl.[7] ........................... A61K 39/12; A61K 51/00
(52) U.S. Cl. ................ 424/204.1; 424/1.73; 536/23.72
(58) Field of Search ................................ 424/204.1, 1.73; 536/23.72

(56) References Cited

FOREIGN PATENT DOCUMENTS

659768 A2 * 5/1994 (EP) .

OTHER PUBLICATIONS

Jansen et al. Vaccine, 1995, vol. 13, No. 16, pp. 1509–1514, 1995.*
Apostolopoulos et al .PNAS USA, 1995, vol. 92, pp. 10128–10132, Oct. 1995.*
Breitburd et al. Journal of Virology, 1995, vol. 69, No. 6, pp. 3959–3963, Jun. 1995.*

* cited by examiner

*Primary Examiner*—Ali R. Salimi
(74) *Attorney, Agent, or Firm*—Joanne M. Giesser; Jack L. Tribble

(57) ABSTRACT

Vaccine formulations comprising recombinant early (E) and late (L) proteins of papillomavirus and oxidized mannan as well as methods of making and using the formulations are provided.

3 Claims, 2 Drawing Sheets

FORMULATIONS OF RECOMBINANT PAPILLOMAVIRUS VACCINES

CROSS-REFERENCE TO RELATED APPLICATIONS

This is a rule 371 application based on the priority date of PCT/US97/23295 filed Dec. 16, 1997, which is a continuation of application Ser. No. 08/992,450 filed Dec. 17, 1997, now abandoned, which claims priority under 35 U.S.C. 119(e) from U.S. Ser. No. 60/033,566, filed Dec. 20, 1996.

STATEMENT REGARDING FEDERALLY-SPONSORED R&D

Not applicable.

REFERENCE TO MICROFICHE APPENDIX

Not applicable.

FIELD OF THE INVENTION

Vaccine formulations comprising recombinant early (E) and late (L) proteins of papillomavirus and oxidized mannan as well as methods of making and using the formulations are provided.

BACKGROUND OF THE INVENTION

The current invention identifies a new technology that may be usefull for eliciting potent cell-mediated and humoral immune responses to a candidate protein antigen for vaccine development.

Aluminum hydroxide generally elicits potent antibody responses to the candidate antigen and little if any cell-mediated immune responses.

Apostolopoulos et al. demonstrated the induction of strong cell-mediated immune responses to mucin 1 antigen (MUC 1) in mice when the animals were immunized with MUC1 antigen conjugated to oxidized mannan (ox-mannan). These studies are described in the following references: i) Production of anti-peptide specific antibody in mice following immunization with peptides conjugated to mannan. Okawa. Y, Howard. C. R. and Steward. M. W. 1992, J immunol. Methods 149: 127–131. Department of clinical sciences, London School of Hygiene and Tropical Medicine, London, UK; ii) Apostolopoulos, V., Pietersz. G. A., Loveland, B. E., Sandrin, M. S., and McKenzie, I. F 1995, Proc. Natl. Acad. Sci. USA, 92: 10128–10132. The Austin Research Institute, Studly Road, Heidelberg 3084, Victoria, Australia; and iii) Apostolopoulos, V., Loveland, B. E., Pietersz. G. A. and McKenzie. I. F. 1995, J Immunol. 155: 5089–5094. The Austin Research Institute, Studly Road, Heidelberg 3084, Victoria, Australia. However, the utility of ox-mannan as an adjuvant or immunomodulator in vaccine development to infectious agents has not been evaluated.

Antigens conjugated to oxidized or reduced mannan are likely to elicit strong cell-mediated and humoral immune responses to the candidate antigen. Alum has been used as an adjuvant that elicits good humoral immune responses and little if any cell-mediated immune responses.

It would be usefull to develop vaccine against human papillomavirus that may require an adjuvant capable of eliciting both humoral and cell-mediated immune responses to papillomavirus antigens. In this report, we describe the utility of ox-mannan in eliciting protective immune responses to infectious agents in cottontail rabbit papillomavirus model.

The human papilloma viruses (HPV) are nonenveloped, double-stranded DNA viruses, with over 75 types identified. Infection with HPV may result in development of genital condylomas and cervical neoplasia, and may be associated with as many as 90% of the cervical carcinomas. The papilloma viruses are species specific with respect to productive infection, and HPV infection in animals does not produce the disease. This necessitates the preliminary testing of candidate vaccines to be carried out in animal papillomavirus models. Cottontail rabbit papillomavirus (CRPV) was the first papillomavirus identified and also the first DNA virus associated with cancers. L1 is the major component of the virus capsid and expression of L1 in baculovirus or yeast results in the formation of virus like particles (VLPs). Immunization of animals with the major capsid protein (L1) VLPs results in the generation of neutralizing antibodies that recognize conformational epitopes formed when viral capsid proteins assemble into VLPs or virions. Although vaccination with VLPs alone is effective against challenge by infectious CRPV, it has no effect in containing pre-existing infection.

In this study we evaluated the utility of oxidized mannan as a carrier for vaccine development and immunotherapy, we conjugated oxidized mannan to CRPV early proteins (E-proteins) antigens expressed in *E. coli* and evaluated their efficacy in containing pre-existing infection.

Papillomavirus infections occur in a variety of animals, including humans, sheep, dogs, cats, rabbits, monkeys, snakes and cows. Papillomaviruses infect epithelial cells, generally inducing benign epithelial or fibroepithelial tumors at the site of infection. Papillomaviruses are species specific infective agents; a human papillomavirus cannot infect a nonhuman animal.

Papillomaviruses may be classified into distinct groups based on the host that they infect. Human papillomaviruses (HPV) are further classified into more than 70 types based on DNA sequence homology (for a review, see Papillomaviruses and Human Cancer, H. Pfister (ed.), CRC Press, Inc., 1990). Papillomavirus types appear to be type-specific immunogens in that a neutralizing immunity to infection to one type of papillomavirus does not confer immunity against another type of papillomavirus.

In humans, different HPV types cause distinct diseases. HPV types 1, 2, 3, 4, 7, 10 and 26–29 cause benign warts in both normal and immunocompromised individuals. HPV types 5, 8, 9, 12, 14, 15, 17, 19–25, 36 and 46–50 cause flat lesions in immunocompromised individuals. HPV types 6, 11, 34, 39, 41–44 and 51–55 cause nonmalignant condylomata of the genital or respiratory mucosa. HPV types 16 and 18 cause epithelial dysplasia of the genital mucosa and are associated with the majority of in situ and invasive carcinomas of the cervix, vagina, vulva and anal canal. HPV6 and HPV11 are the causative agents for more than 90% of all condyloma (genital warts) and laryngeal papillomas. The most abundant subtype of HPV type 6 is HPV6a.

Immunological studies in animals have shown that the production of neutralizing antibodies to papillomavirus antigens prevents infection with the homologous virus. The development of effective papillomavirus vaccines has been slowed by difficulties associated with the cultivation of papillomaviruses in vitro. The development of an effective HPV vaccine has been particularly slowed by the absence of a suitable animal model.

Neutralization of papillomavirus by antibodies appears to be type-specific and dependent upon conformational epitopes on the surface of the virus.

Paprnomaviruses are small (50–60 nm), nonenveloped, icosahedral DNA viruses that encode for up to eight early and two late genes. The open reading frames (ORFs) of the virus genomes are designated E1 to E7 and L1 and L2, where "E" denotes early and "L" denotes late. L1 and L2 code for virus capsid proteins. The early (E) genes are associated with functions such as viral replication and cellular transformation.

The L1 protein is the major capsid protein and has a molecular weight of 55–60 kDa. L2 protein is a minor capsid protein which has a predicted molecular weight of 55–60 kDa and an apparent molecular weight of 75–100 kDa as determined by polyacrylamide gel electrophoresis. Immunologic data suggest that most but not all of the L2 protein is internal to the L1 protein. The L2 proteins are highly conserved among different papillomaviruses, especially the 10 basic amino acids at the C-terminus. The L1 ORF is highly conserved among different papillomaviruses.

The L1 and L2 genes have been used to generate vaccines for the prevention of papillomavirus infections in animals. Zhou et al., (1991; 1992) cloned HPV type 16 L1 and L2 genes into a vaccinia virus vector and infected CV-1 mammalian cells with the recombinant vector to produce virus-like particles (VLP). Bacterially-derived recombinant bovine papillomavirus L1 and L2 have been generated. Neutralizing sera to the recombinant bacterial proteins cross-reacted with native virus at low levels, presumably due to differences in the conformations of the native and bacterially-derived proteins.

Recombinant baculoviruses expressing HPV6 L1, HPV11 L1, HPV16 L1, HPV18 L1, HPV31 L1 or HPV16 L2 ORFs have been used to infect insect SF9 cells and produce L1 and L2 proteins. Western blot analyses showed that the baculovirus-derived L1 and L2 proteins reacted with antibody to HPV16. The baculovirus derived L1 forms VLPs.

Carter et al., (1991) demonstrated the production of HPV 16 L1 and HPV16 L2 proteins by recombinant strains of *Saccharomyces cerevisiae*. Carter et al. also demonstrated the production of HPV6b L1 and L2 proteins. The HPV6b L1 protein was not full-length L1 protein. The recombinant proteins were produced as intracellular as well as secreted products. The recombinant L1 and L2 proteins were of molecular weights similar to the native proteins. When the proteins were expressed intracellularly, the majority of the protein was found to be insoluble when the cells were lysed in the absence of denaturing reagents. Although this insolubility may facilitate purification of the protein, it may hamper analysis of the native epitopes of the protein.

Recombinant proteins secreted from yeast were shown to contain yeast-derived carbohydrates. The presence of these N-linked oligosaccharides may mask native epitopes. In addition, the secreted recombinant proteins may contain other modifications, such as retention of the secretory leader sequence.

It would be useful to develop methods of producing large quantities of papillomavirus proteins of any species and type by cultivation of recombinant yeasts. It would also be useful to produce large quantities of papillomavirus proteins having the immunity-conferring properties of the native proteins, such as the conformation of the native protein.

The present invention is directed to recombinant papillomavirus proteins having the immunity conferring properties of the native papillomavirus proteins as well as methods for their production and use. The present invention is directed to the production of a prophylactic and therapeutic vaccine for papillomavirus infection. The recombinant late proteins of the present invention are capable of forming virus-like particles. These VLP are immunogenic and prevent formation of warts in an animal model. In addition, recombinant E-proteins are produced in *E. coli* and these proteins are presented so as to elicit a cell-mediated immune response. The present invention uses the cottontail rabbit papillomavirus (CRPV) and HPV type 6 (subtype 6a) as model systems.

SUMMARY OF THE INVENTION

Vaccine formulations comprising recombinant and early (E) proteins adducted to oxidized mannan and late (L) proteins of papillomavirus and oxidized mannan as well as methods of making and using the formulations are provided.

BRIEF DESCRIPTION OF THE DRAWINGS

Figures show that CRPV infection resulted in development of warts at all challenge sites in control animals. Development of papillomas was inhibited >90% in 3/3 animals of group 4 animals immunized with VLPs in combination with E-proteins conjugated to oxidized mannan. In contrast, only 3/5 animals of group 2, immunized with VLPs+E-protein mixture in RIBI and 2/4 animals of group 2 immunized with VLPs+Ox-mann-E-protein mixture in RIBI showed >90% inhibition of papilloma development. Results suggest that the immunization of rabbits with E-protein cocktail conjugated to oxidized mannan in combination with L1/L2 VLPs causes significant inhibition of wart development of CRPV infected cells.

DETAILED DESCRIPTION OF THE INVENTION

Figure 1:
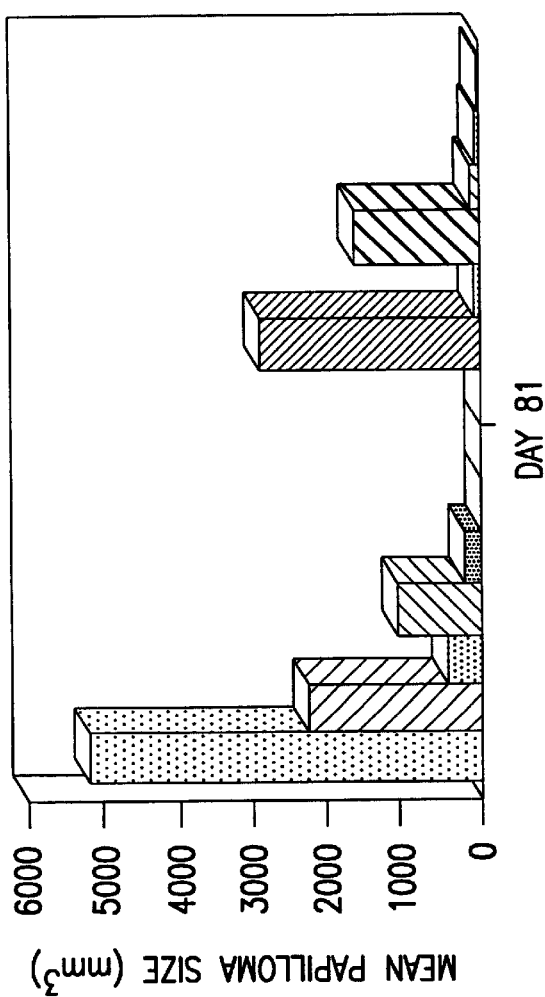
FIG. 1. Immunization of rabbits with E-protein cocktail in combination with L1/L2 VLPS inhibits CRPV induced papilloma development.
Figure 1:
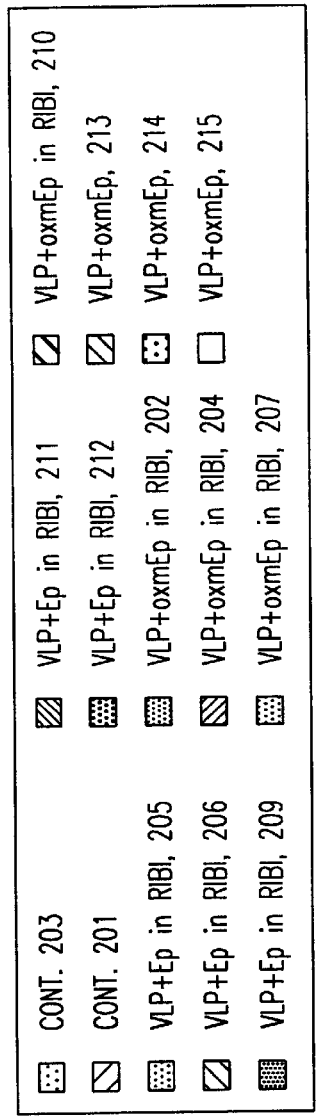
Figure 2:
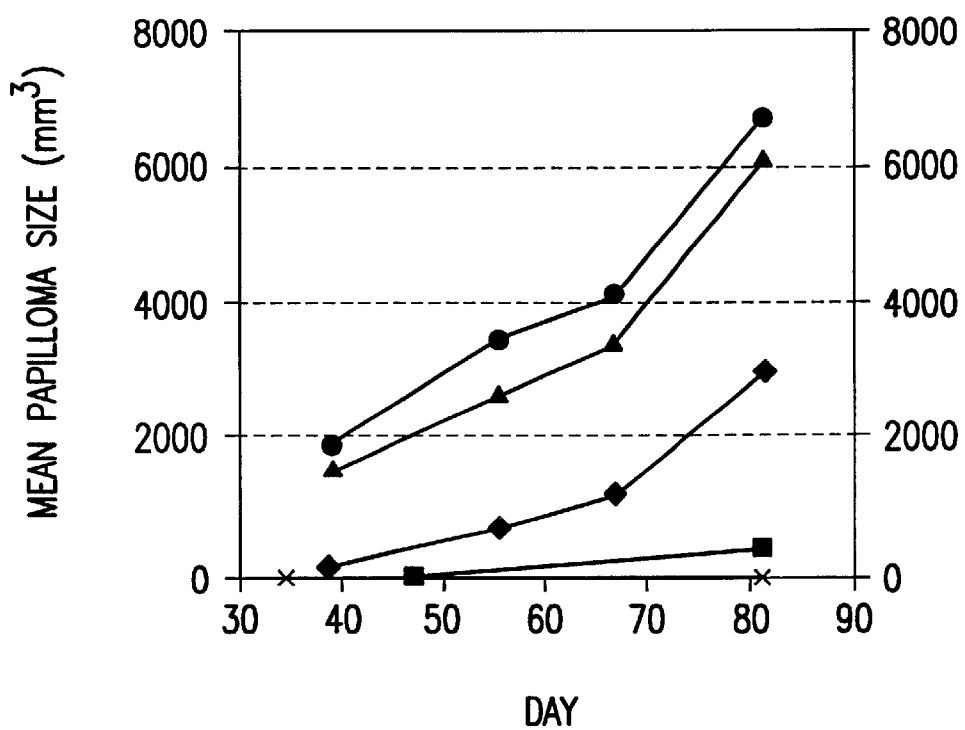
FIG. 2. Comparison of formulation on CRPV induced papillon a development.

Vaccine formulations comprising recombinant early (E) and late (L) proteins of papillomavirus and oxidized mannan as well as methods of making and using the formulations are provided.

The current invention identifies a new technology that may be useful for eliciting potent cell-mediated and humoral immune responses to a candidate protein antigen for vaccine development.

Aluminum hydroxide generally elicits potent antibody responses to the candidate antigen and little if any cell-mediated immune responses.

Apostolopoulos et al. demonstrated the induction of strong cell-mediated immune responses to mucin 1 antigen (MUC 1) in mice when the animals were immunized with MUC1 antigen conjugated to oxidized mannan (ox-mannan). However, the utility of ox-mannan as an adjuvant or immunomodulator in vaccine development to infectious agents has not been evaluated.

Antigens conjugated to oxidized or reduced mannan are likely to elicit strong cell-mediated and humoral immune responses to the candidate antigen. Alum has been used as an adjuvant that elicits good humoral immune responses and little if any cell-mediated immune responses.

A vaccine against human papillomavirus that may require an adjuvant capable of eliciting both humoral and cell-mediated immune responses to papillomavirus antigens. In this report, we describe the utility of ox-mannan in eliciting protective immune responses to infectious agents in cottontail rabbit papillomavirus model.

In this study we evaluated the utility of oxidized mannan as a carrier for vaccine development and immunotherapy, we conjugated oxidized mannan to, E. coli expressed recombinant CRPV early proteins (E-proteins) antigens and evaluated their efficacy in containing pre-existing infection.

Methods, compositions and processes for the prevention, characterization, detection and treatment of papifiomavirus (PV) infection are provided. The methods are based on the production of recombinant L1 or recombinant L2 or recombinant L1 and L2 proteins in yeast. The recombinant proteins are capable of mimicking the conformational neutralizing epitopes of native PV. The recombinant L1 or L1 and L2 proteins may also be capable of forming virus-like particles (VLP). The compositions of the invention include but are not limited to recombinant DNA molecules encoding the L1 or L2 or L1 and L2 proteins, the recombinant proteins either alone or in combination with other recombinant proteins, VLP comprised of at least one recombinant protein, fragments of the recombinant proteins, pharmaceutical compositions comprising the recombinant proteins, vaccine compositions comprising the recombinant proteins, antibodies to the recombinant proteins or VLP, immunogenic compositions comprising at least one recombinant protein, and diagnostic kits comprising the recombinant DNA molecules or the recombinant proteins. The processes of the present invention include but are not limited to the process of producing a recombinant protein comprising the transformation of an appropriate yeast host cell with a recombinant DNA molecule, cultivating the transformed yeast under conditions that permit the expression of the DNA encoding the recombinant protein, and purifying the recombinant protein. The processes of the present invention also include the administration of the recombinant protein, recombinant protein compositions or VLP to an animal, including but not limited to humans. Appropriate host cells include, but are not limited yeast strains of the genera Saccharomyces, Pichia, ulyermyces, Schizosaccharomyces and Hansenula.

Immunological studies in animals have shown that the production of neutralizing antibodies to papillomavirus capsid proteins prevents infection with the homologous virus. The development of effective papillomavirus vaccines has been slowed by difficulties associated with the cultivation of papillomaviruses in vitro. The development of an effective HPV vaccine has been particularly slowed by the absence of a suitable animal model.

Neutralization of papillomavirus by antibodies appears to be type-specific and dependent upon conformational epitopes on the surface of the virus.

Pharmaceutically useful compositions comprising the proteins or VLP may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein or VLP. Such compositions may contain proteins or VLP derived from more than one type of HPV.

Therapeutic or diagnostic compositions of the invention are administered to an individual in amounts sufficient to treat or diagnose PV infections. The effective amount may vary according to a variety of factors such as the individual's condition, weight, sex and age. Other factors include the mode of administration. Generally, the compositions will be administered in dosages ranging from about 1 µg to about 250 µg.

The pharmaceutical compositions may be provided to the individual by a variety of routes such as subcutaneous, topical, oral, mucosal, and intramuscular.

The vaccines of the invention comprise recombinant proteins or VLP that contain the antigenic determinants necessary to induce the formation of neutralizing antibodies in the host. Such vaccines are also safe enough to be administered without danger of clinical infection; do not have toxic side effects; can be administered by an effective route; are stable; and are compatible with vaccine carriers.

The vaccines may be administered by a variety of routes, such as orally, parenterally, subcutaneously, mucosally or intramuscularly. The dosage administered may vary with the condition, sex, weight, and age of the individual; the route of administration; and the type PV of the vaccine. The vaccine may be used in dosage forms such as capsules, suspensions, elixirs, or liquid solutions. The vaccine may be formulated with an immunologically acceptable carrier.

The vaccines are administered in therapeutically effective amounts, that is, in amounts sufficient to generate a immunologically protective response. The therapeutically effective amount may vary according to the type of PV. The vaccine may be administered in single or multiple doses.

The methods of the present invention make possible the formulation of subviral vaccines for preventing PV infection. Using the methods, either monovalent or multivalent PV vaccines may be made. For example, a monovalent HPV type 16 vaccine may be made by formulating recombinant HPV 16 L1 protein or L2 protein or L1 and L2 proteins. Alternatively, a multivalent HPV vaccine may be formulated by mixing L1 or L2 or L1 and L2 proteins or VLP from different HPV types.

The recombinant proteins and VLP of the present invention may be used in the formulation of immunogenic compositions. Such compositions, when introduced into a suitable host, are capable of inducing an immunologic response in the host.

The recombinant proteins and VLP may be used to generate antibodies. The term "antibody" as used herein includes both polyclonal and monoclonal antibodies, as well as fragments thereof, such as, Fv, Fab and F(ab)2 fragments that are capable of binding antigen or hapten.

The recombinant proteins, VLP and antibodies of the present invention may be used to serotype HPV infection and HPV screening. The recombinant proteins, VLP and antibodies lend themselves to the formulation of kits suitable for the detection and serotyping of HPV. Such a kit would comprise a compartmentalized carrier suitable to hold in close confinement at least one container. The carrier would further comprise reagents such as recombinant HPV protein or VLP or anti-HPV antibodies suitable for detecting a variety of HPV types. The carrier may also contain means for detection such as labeled antigen or enzyme substrates or the like.

The recombinant proteins and VLP of the present invention are also useful as molecular weight and molecular size markers.

The following examples are provided to further define the invention without, however, limiting the invention to the particulars of these examples.

EXAMPLE 1

Expression of CRPV E1, E2, E4, E5, E6 and E7 genes in E. coli

PCR primers based on the published sequence of CRPV (Yaniv, M. et al. Proc. Natl. Acad. Sci. U.S.A., 82, 1580–1584, 1985) were used to PCR amplify the full length CRPV E1, E2, E4, E5, E6 and E7 genes. To enhance expression of CRPV E4 protein, the first 4 amino acid codons of CRPV E1 protein were fused to the amino terminal portion of E4 using PCR (E1Ô4). The open-reading frames of E6 and E7 genes were fused at the carboxy terminus of E6 with the amino terminus of E7 using PCR. All PCR amplified products were subcloned into the vector pQE30 (Qiagen, Inc., San Diego, Calif.) and sequenced. Expression of the desired protein was carried out by growing 1 liter cultures of $E.$ $coli$ SG-1300 expressing desired E-proteins for eight hours at 37° C. in LB media and then induced overnight at 30° C. using 1 mM IPTG. The cells were then collected by centrifugation for 15 min at 5000 rpm, washed with 500 ml of PBS and the E proteins were purified using the manufacturer's directions (Qiagen, Inc.).

EXAMPLE 2

Purification CRPV E-proteins $E.$ $coli$ culture paste (from 1 liter of medium) was solubilized in 100 mL of extraction buffer (6.0 M Guanidine Hydrochloride, 2 mM imidazole, and 0.35 mM 2 β-mercaptoethanol, 0.1 M Sodium Phosphate pH 7.4) at room temperature for 30 minutes. The soluble fraction was isolated by centrifuigation at 18000×g for 30 minutes and was mixed with 8.0 mL of packed Ni resin equilibrated with the extraction buffer. The resin slurry was rotated for 2 hours at room temperature or 16 hours at 4° C. The unbound proteins were removed by centrifugation at 200×g. Resin was washed with 4.0 volumes each of extraction buffer and buffer A (8.0 M urea, 0.1 M sodium phosphatem pH 7.4) at room temperature. Resin was resuspended in buffer A pH 6.3 and was transferred to a column and was washed sequentially with 4 volumes of buffer B (8.0 M urea, 10 mM imidazole, 0.1 M sodium phosphate, pH 6.3), buffer C (8.0M urea, 200 mM imidazole, 0.1 M sodium phosphate, pH 6.3) buffer D (8.0 M urea, 500 mM imidazole, sodium phosphate pH 5.7) and finally with buffer E (8.0 M urea, 1.0 M imidazole, 0.1 M sodium phosphate, pH 5.7). Purified protein eluted in buffer C, D & F. Protein was quantitated with Bradford or BCA protein assays and analyzed by SDS-PAGE and western blotting. Purified proteins were extensively dialyzed with deionized water to remove urea before conjugation or other formulations (Qiagen Inc. Manual).

EXAMPLE 3

Expression of CRPV L1 and L2 Genes as Virus Like Particles (VLPs)

PCR primers based on the published sequence of CRPV (Yaniv, M. et al. Proc. Natl. Acad. Sci. U.S.A., 82, 1580–1584, 1985) were used to PCR amplif y the full length CRPV L1 gene and a CRPV L2 gene that had the first 37 codons (111 bp) deleted. These genes were subcloned into the 2 cassette vector pAcUW51 (PharMingen Inc., San Diego, Calif.) for co-expression in the baculovirus expression system or into a 2 cassette vector pLS110 (Hofinaun, K J. et al. J Virol 209:506–518, 1995) for expression in yeast. The pAcUVW51 vector containing the genes encoding CRPV L1 and L2 proteins was transfected into SF9 cells using the PharMingen Baculogold expression kit. Supernatants from this transfection were used to infect large cultures (1 Liter) of Sf9 cells which were grown for 5 days, the cells were collected and the L1/L2 VLPs were purified.

The pLS110 vector containing the genes encoding CRPV L1 and L2 proteins was transformed into yeast using the standard spheroplast transformation protocol. Positive clones were identified and large scale cultures were grown. 200 ml cultures of yeast expressing L1/L2 VLPs were grown for 2 days at 30° C. This 200 ml culture was then used to inoculate 1 liter of induction medium (2% yeast extract, 1% soy peptone, 1.6% glucose, 4% galactose) which was grown at 30° C. for 5 days. The cells were collected by centrifugation and the L1/L2 VLPs were purified.

EXAMPLE 4

Conjugation of Mannan to E-proteins

*E. coli* expressed CRPV E-proteins were purified by affinity chromatography on Ni-coluamn and were extensively dialyzed against de-ionized water. CRPV E-proteins were mixed (E1, E2, E6̂07 150 ug of each; E1̂04 100 ug and E5 50 ug per dose) and lyophilized. 14 mg of mannan (purified from Saccaharomyces SIGMA Chemical Co.) was dissolved in 1.0 mL of 0.1M phosphate buffer pH 6.0, mixed with 20 uL of 0.1M sodium periodate and incubated for 1 hr at 4° C. Ethanediol (20 uL) was added and incubated for a further 30 minutes at 4° C. and the mixture was passed through a PD-10 column equilibrated in bicarbonate buffer pH 8.0 (Apostolopoulos. V. et al. Proc. Natl. Acad. Sci. USA, 92: 10128–10132, 1995). The oxidized mannan that eluted in void volume was mixed with lyophilized E-proteins mixture and incubated at room temperature over night and used.

EXAMPLE 5

Conjugation of Mannan to E-proteins

*E. coli* expressed CRPV E-proteins were purified by affinity chromatography on Ni-column and were extensively dialyzed against de-ionized water. CRPV E-proteins were mixed (E1, E2, E6̂07 150 ug of each; E1̂04 100 ug and E5 50 ug per dose) and lyophilized. 14 mg of mannan (purified from Saccaharomyces, Sigma ) was dissolved in 1.0 mL of 0.1 M phosphate buffer pH 6.0, mixed with 20 uL of 0.1M sodium periodate and incubated for 1 hr at 4° C. Ethanediol (20 uL) was added and incubated for a further 30 minutes at 4° C. and the mixture was then passed through a PD-10 column equilibrated in bicarbonate buffer (0.02 M, pH 8.0). The oxidized mannan that eluted in void volume was mixed with lyophilized E-proteins mixture and incubated at room temperature overnight.

EXAMPLE 6

Evaluation of Ox-mannan-E-protein Vaccine in CRPV Model

Five rabbits were immunized with 25 ug of yeast-derived L1/L2 VLPs with 150 ug of each E1, E2, E1̂04, E6̂07 and 50 g of E5 CRPV E-proteins in RIBI (group 1). Four rabbits were immunized with the same mixture in RIBI except the E-proteins were conjugated to the oxidized polysaccharide mannan (Ox-mann-E-protein, group 2). Three rabbits each received RIBI only (group 3) or L1/L2 VLPs+Ox-mann-E-protein without RIBI (group 4). Each rabbit received 0.3 ml each intramuscularly into each hind leg, 0.05 ml each intradermally at 6 sites and 0.1 ml subcutaneously in the neck of the desired formulation. Rabbits were infected with cottontail rabbit papillomavirus (CRPV) 4 days after the first immunization and boosted with the same amount of antigen in the same formulation on day 21 and day 42. Size of the papillomas was determined on day 35 and day 47 post infection.

EXAMPLE 7

Results

CRPV infection resulted in development of warts at all challenge sites in control animals. Development of papillomas was inhibited >90% in 3/3 group 4 animals immunized with VLPs+Oxmann-E-protein mixture without RIBI. In contrast, only 3/5 animals of group 1, immunized with VLPs+E-protein mixture in RIBI and 2/4 animals of group 2 immunized with VLPs+Ox-mann-E-protein mixture in RIBI showed >90% inhibition of papilloma development. The Inhibition of papilloma development in the remaining 2 animals of group 1 was 80% in group 2 ranged from 10–50%. Results suggest that the immunization of rabbits with E-protein cocktail in combination with L1/L2 VLPs in RIBI causes significant (80–90%) inhibition of wart development. Interestingly similar inhibition of wart development was also observed in animals immunized with the formulation that contained only VLPs and E-protein cocktail conjugated to oxidized mannan (FIG. 1).

What is claimed:

1. A method of preventing infection of an animal by a papillomavirus comprising administration of a mixture comprising recombinant papillomavirus virus-like particles, recombinant papillomavirus E proteins and oxidized mannan (ox-mannan) to the animal.

2. An immunogenic composition comprising ox-mannan, recombinant papillomavirus virus-like particles and recombinant papillomavirus E proteins.

3. A vaccine comprising ox-mannan, recombinant papillomavirus virus-like particles and recombinant papillomavirus E proteins.

* * * * *